US008141555B1

(12) United States Patent
Neusch et al.

(10) Patent No.: US 8,141,555 B1
(45) Date of Patent: Mar. 27, 2012

(54) BACKBOARD COVER AND ASSOCIATED METHODS

(76) Inventors: Scott R. Neusch, Debary, FL (US); Mark T. Steinert, Winter Park, FL (US)

( * ) Notice: Subject to any disclaimer, the term of this patent is extended or adjusted under 35 U.S.C. 154(b) by 598 days.

(21) Appl. No.: 12/204,054

(22) Filed: Sep. 4, 2008

Related U.S. Application Data

(60) Provisional application No. 60/974,166, filed on Sep. 21, 2007, provisional application No. 60/989,504, filed on Nov. 21, 2007.

(51) Int. Cl.
*A61F 5/37* (2006.01)
*A61B 19/00* (2006.01)

(52) U.S. Cl. ......................... 128/872; 128/869; 128/870

(58) Field of Classification Search .................. 128/848, 128/849, 872, 870, 869; 5/626, 625, 691, 5/621, 623, 624, 622; 4/497
See application file for complete search history.

(56) References Cited

U.S. PATENT DOCUMENTS 1,959,920 A 5/1934 Kaiser
2,810,921 A * 10/1957 Seidenberg ........................ 5/501
3,956,782 A * 5/1976 Morrison ........................... 5/737
4,877,288 A 10/1989 Lee
4,905,712 A 3/1990 Bowlin et al.
4,924,543 A 5/1990 Hoss et al.
4,979,520 A 12/1990 Boone et al.
4,993,092 A * 2/1991 Weeks .............................. 5/658
5,088,137 A 2/1992 Rose
5,179,746 A * 1/1993 Rogers ............................... 5/625
5,513,655 A * 5/1996 Peimer et al. ................. 128/849
5,615,425 A 4/1997 Corente
5,819,746 A 10/1998 Walton
6,170,486 B1 * 1/2001 Islava ............................ 128/869
6,899,662 B2 * 5/2005 Gamble et al. ................ 482/142
7,100,226 B1 9/2006 Walton
2004/0084053 A1 5/2004 Hess
2006/0230535 A1 10/2006 Cox
2007/0056096 A1 3/2007 Assink
2007/0157935 A1 7/2007 Reynolds

* cited by examiner

*Primary Examiner* — Patricia Bianco
*Assistant Examiner* — Ophelia Hawthorne
(74) *Attorney, Agent, or Firm* — Allen, Dyer, Doppelt, Milbrath & Gilchrist, P.A.

(57) ABSTRACT

A backboard cover includes a sheet of flexible material having an upper portion for covering a backboard top surface. The sheet has a lower surface with a non-skid region for retaining the sheet's upper portion in position atop the backboard. The sheet has a plurality of apertures positioned and dimensioned for communicating with handholds in the backboard. The sheet has a portion that can extend over to the bottom surface of the backboard, for retaining the sheet on the backboard. The backboard cover further includes an absorbent pad affixed atop the sheet for absorbing and retaining bodily or other fluids that may be exuded during the patient's residence thereon. An affixing element such as, but not intended to be limited to, a hook-and-latch pad, is affixed adjacent a top edge of the sheet, for serving as a fixation site for at least a pillow thereto.

24 Claims, 4 Drawing Sheets

BACKBOARD COVER AND ASSOCIATED METHODS

CROSS-REFERENCE TO RELATED APPLICATION

This application claims priority to provisional application Ser. No. 60/974,166, filed Sep. 21, 2007 and to provisional application Ser. No. 60/989,504, filed Nov. 21, 2007.

BACKGROUND OF THE INVENTION

1. Field of the Invention

The present invention relates to devices and methods for supporting and transporting an injured person, and, more particularly, to such devices and methods for covering backboards for these purposes.

2. Description of Related Art

A typical backboard used for supporting and transporting an injured person comprises a re-usable 16 or 18-in.×72-in. board having a plurality of hand-hold apertures arrayed along each side, and also adjacent the top and the bottom edge. It is known to affix a cervical immobilization device (CID) atop the backboard that comprises styrofoam head blocks, a chin strap, a head strap, and a padded base unit for restraining the head and neck from moving.

A particular problem with this device and method is that, between uses, the backboards may not be cleaned sufficiently, leaving contaminants such as bodily fluids, petroleum products, microbes, and adhesive residue from the CIDs, which is difficult to remove without compromising the protective coating on the backboard. Further, multiple backboards may be stored atop one another, thereby raising the potential of transferring contaminants between them.

It would therefore be desirable to provide a device and method that could maintain a backboard in a more sanitary state after usage, and thereby alleviate this potential for transmitting the contaminant to the next user(s) or to the medical personnel handling the backboard.

SUMMARY OF THE INVENTION

The present invention is directed to a backboard cover, and to a method of making, and a method of using same. The backboard cover comprises a sheet of flexible material formed to have an upper portion dimensioned for covering a backboard top surface. The sheet further has a lower surface comprising means for retaining the sheet's upper portion in position atop the backboard.

The sheet additionally has a plurality of apertures, at least some of which are positioned and dimensioned for communicating with handholds in the backboard. The sheet also has means for extending over to the bottom surface of the backboard, for retaining the sheet on the backboard.

The backboard cover further comprises an absorbent pad affixed atop the sheet for absorbing and retaining bodily or other fluids that may be exuded during the patient's residence thereon. An affixing means such as, but not intended to be limited to, a hook-and-latch pad, is affixed adjacent a top edge of the sheet, for serving as a fixation site for at least a pillow thereto.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
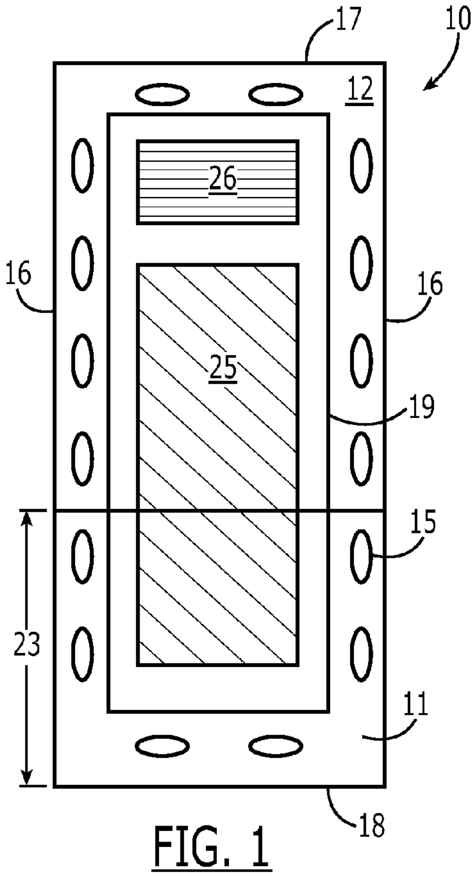
FIG. 1 is a top plan view of a backboard cover sheet of the present invention.
Figure 2:
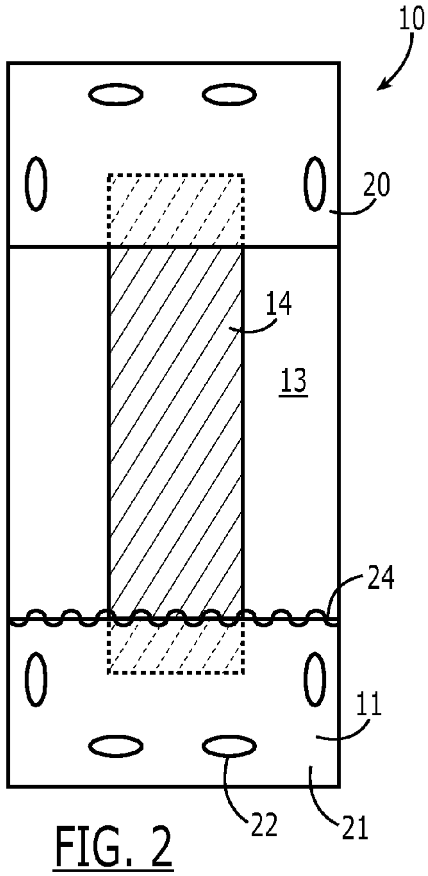
FIG. 2 is a bottom plan view of the backboard cover sheet of FIG. 1.

A description of the preferred embodiments of the present invention will now be presented with reference to FIGS. 1-9.

A backboard cover 10 of the present invention can comprise a disposable sheet of flexible material 11 that is formed to have an upper portion 12 (FIG. 1) dimensioned for covering a backboard top surface. A typical backboard known in the art can be 16 or 18 in. wide and 72 in. long, although this is not intended as a limitation, and in some cases the width can be up to 30 in. or more. The sheet 11 can comprise a material such as polypropylene, although this is not intended as a limitation.

The sheet upper portion 12 has a rear surface 13 (FIG. 2) comprising means for resisting a shifting of the sheet's upper portion 12 relative to the backboard. Such means can comprise, for example, a non-skid element 14 either affixed to or integral with the rear surface 13, such as rubberized elements as are known for use with bedroom slippers and the like.

The sheet 11 additionally has a plurality of apertures, or slots 15, that are positioned and dimensioned in alignment with handholds in the backboard, along both sides 16 and along the top 17 and bottom 18 edges. The slots 15 can comprise, for example, perforated regions in the sheet 11 that can be "punched through" for use. In order to keep the slots 15 from further tearing, a reinforcing element such as a stitched border 19 inside the slots 15 can be present.

The sheet 11 also has a lower portion comprising means for extending over to a bottom surface of the backboard, for retaining the sheet 11 on the backboard. Such a retention means can comprise, for example, upper 20 and lower 21 pockets formed or integral with the upper portion 12, as are known in the art for retaining pillows, for example. The pockets 20,21 also can have slots 22 therein for communication with the backboard handholds. One of the pockets 20,21 can also serve as a self-containment element after use, by stuffing the cover 10 inside one of the pockets 20,21 to contain any biohazard material on the cover 10.

Further, some or all of the sheet 11 can comprise a stretchable material to enhance fitting with the backboard. As an example, a region 23 comprising a lower 18 in. of the sheet's upper portion 12 can comprise such a material. In addition to this, or as an alternative thereto, an elasticized inner edge 24, such as used with fitted sheets, can be provided to achieve an optimal fit.

The backboard cover 10 of the present invention further comprises an absorbent pad 25 affixed atop the sheet's upper portion 12 for absorbing and retaining bodily or other fluids that may be exuded during the patient's residence thereon. An affixing means such as, but not intended to be limited to, a hook-and-latch pad 26, is also affixed adjacent the top edge 17 of the sheet 11, for serving as a fixation site, as will be discussed in the following.

Figure 3:
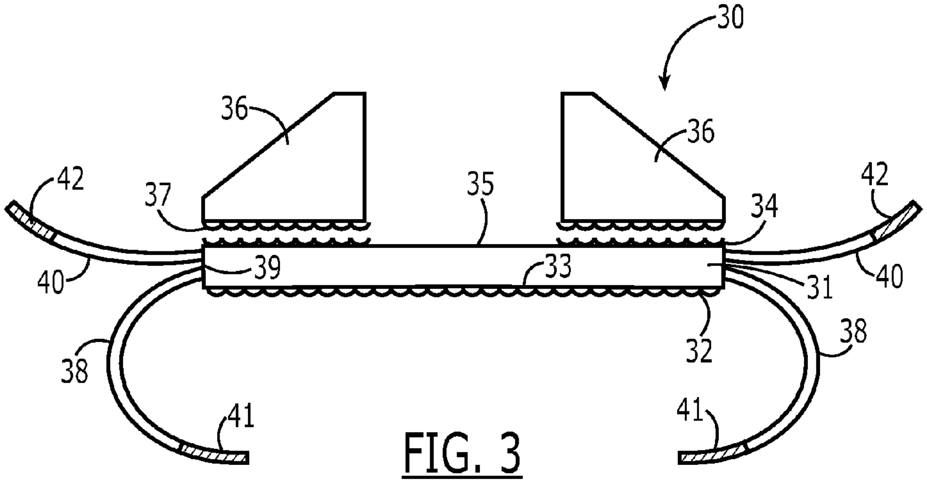
FIG. 3 is an exploded view of an exemplary cervical immobilization device for use with the backboard cover sheet of FIG. 1.
Figure 4:
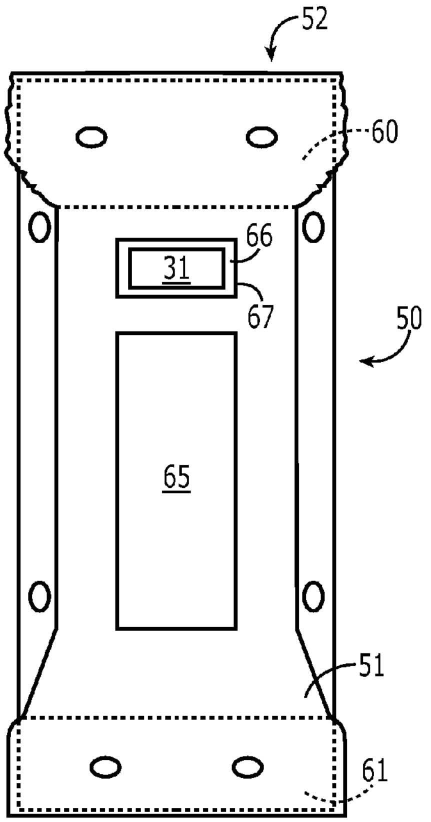
FIG. 4 is a top plan view of an alternate embodiment of a backboard cover sheet positioned on a backboard.
Figure 5:
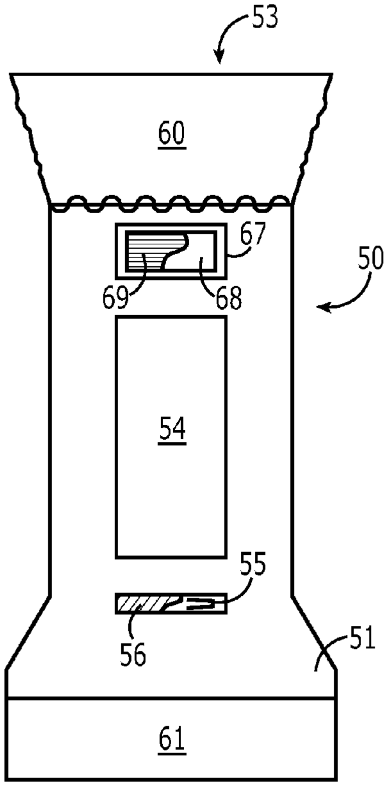
FIG. 5 is a bottom plan view of the backboard cover sheet of FIG. 4.
Figure 6:
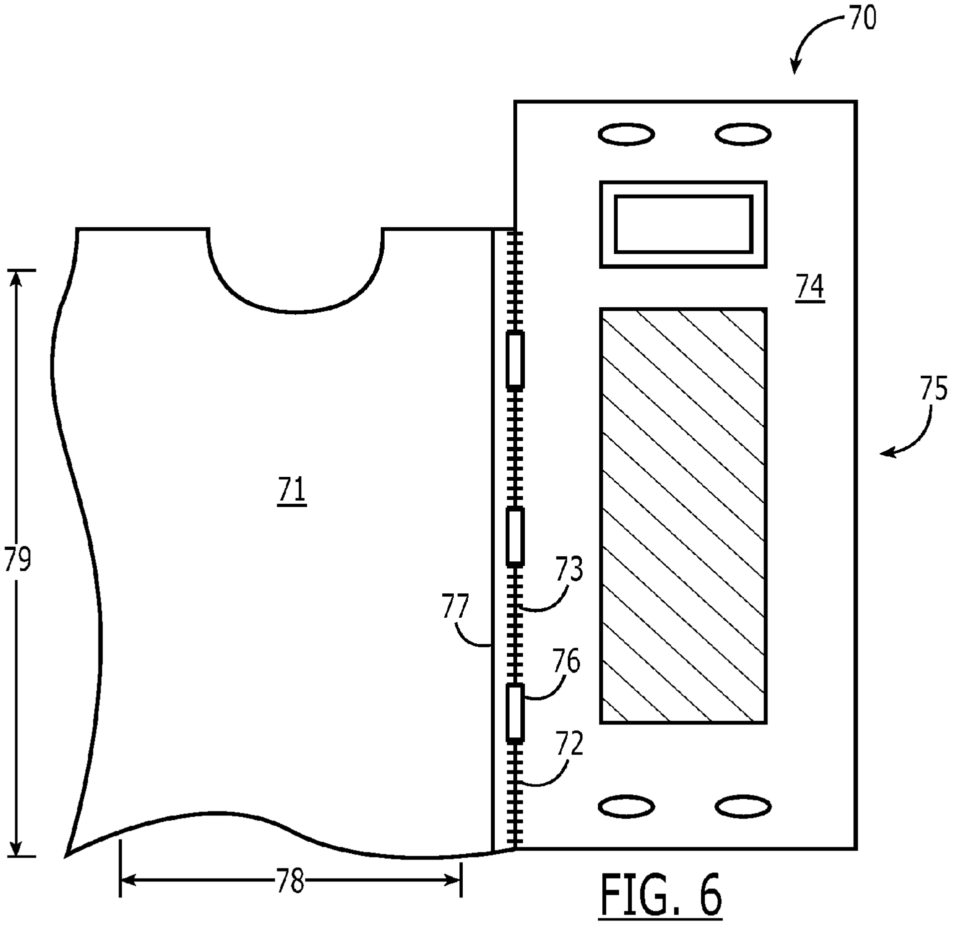
FIG. 6 is a top plan view of a backboard cover having a blanket attached.
Figure 7:
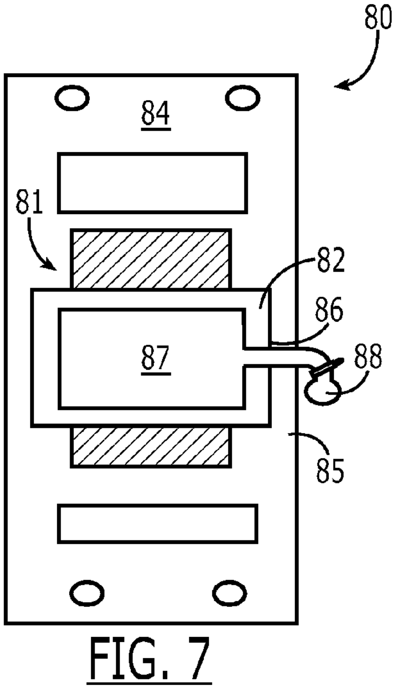
FIG. 7 is a bottom plan view of a backboard cover having a lumbar support system.
Figure 8:
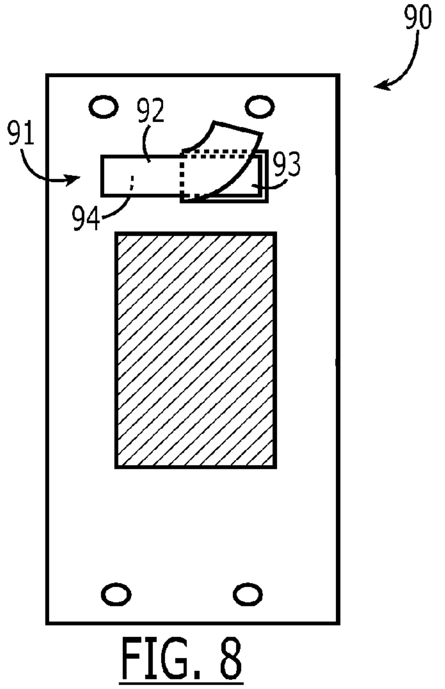
FIG. 8 is a top plan view of a backboard cover having a feature for attaching a cervical immobilization device thereto.
Figure 9:
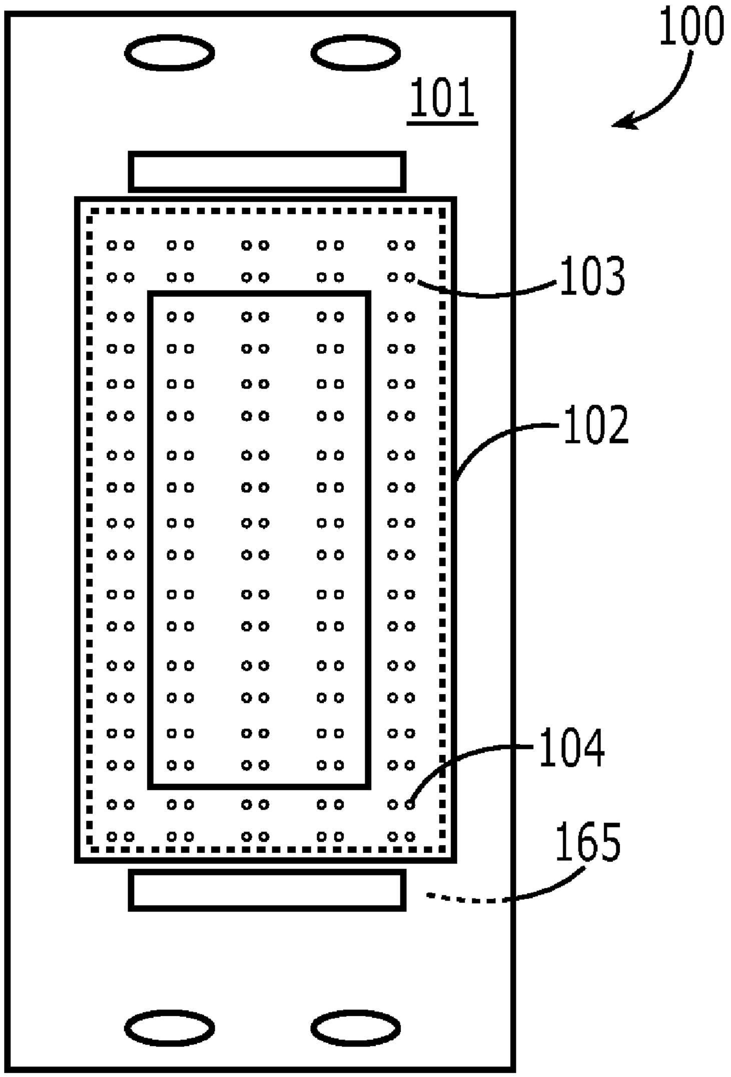
FIG. 9 is a bottom plan view of a backboard cover having a supporting feature.

Another feature of the cover 10 comprises an enhanced cervical immobilization device (CID) 30 (FIG. 3). The CID 30 comprises a base/pillow 31 that is affixable via a hook-and-latch element 32 on its bottom surface 33, for example, to the pad 26 on the sheet 11. The pillow 31 itself has a fixation element such as a hook-and-latch element 34 on a top surface 35 thereof, to which are affixable via a corresponding hook-and-latch element 37 a pair of head restraints 36 for immobilizing the patient's head. Two portions of a chin strap 38 extend from the pillow's sides 39. Finally, two portions of a secondary strap 40 extend from the pillow's sides 39, above the chin strap portions 38. This secondary strap 40 can be used, for example, to maintain an oxygen line or an intubation device in place, permitting such to be quickly positioned on or in the patient without moving the patient's head substantially, and without using tape on the patient's face. Both straps' portions 37,39 are affixable together respectively, via hook-and-latch regions 40,41 thereon.

In another embodiment, believed at the time of filing to represent a preferred embodiment, a backboard cover 50 can comprise a disposable sheet of flexible material 51 that is formed to have an upper portion 52 (FIG. 4) dimensioned for covering a longitudinally central portion of a backboard top surface. The sheet 51 can comprise a material such as polypropylene, although this is not intended as a limitation, and have a width of approximately 16-18 in.

The sheet 51 further has a lower surface 53 (FIG. 5) comprising means for resisting a shifting of the sheet's upper portion 52 relative to the backboard. Such means can comprise, for example, a non-skid element 54 either affixed to or integral with the lower surface 53, as described above. In addition to, or instead of, the non-skid element 54 can be provided an adhesive element 55 covered with a backing sheet 56, to provide additional resistance to slippage during use.

The sheet 51 in this embodiment 50 has a width along a central portion that does not extend to encompass the handholds in the backboard; so neither slots nor stitching is needed in this embodiment 50.

The sheet 51 also has means for extending over to a bottom surface of the backboard, for retaining the sheet 51 on the backboard. Such a retention means can comprise, for example, the sheet 51 flaring outward to a width sufficient to encompass the backboard. Upper 60 and lower 61 pockets are formed or integral with the upper portion 52. The pockets 60,61 again do not require slots for communication with the backboard handholds owing to the reduced width of this embodiment 50. In this embodiment the upper pocket 60 is elasticized for placement around the backboard's upper end. The lower pocket 61 can be slid onto the backboard's lower end first and does not need to be elasticized.

One of the pockets 60,61 can also serve as a self-containment element after use, by stuffing the cover 50 inside one of the pockets 60,61 to contain any biohazard material on the cover 50. Alternatively, or in addition to this use, another container can be provided for storing both an unused and a used cover 50, such as a fluid-impermeable zipper-type enclosure bag. Further, some or all of the sheet 51 can comprise a stretchable material to enhance fitting with the backboard.

The backboard cover 50 of the present invention further comprises an absorbent pad 65 affixed atop the sheet's upper portion 52 for absorbing and retaining bodily or other fluids that may be exuded during the patient's residence thereon.

The sheet 51 additionally has an aperture 66 cut therethrough from the upper portion 52 through to the lower surface 53. Affixed around the edges 67 of the aperture 66 is the base 31 of the CID 30 as discussed above, which has an adhesive layer 68 covered by a backing sheet 69. In use, then, the backing sheet 69 is removed, exposing the adhesive layer 68, and the CID base 31 is attached directly to the backboard.

Another embodiment of a backboard cover 70 (FIG. 6) has a blanket 71 incorporated thereinto, wherein the blanket 71 is affixed via, for example, stitching 72 along a first side 73 of the cover 71 and is placeable over a top surface 74 of the cover base 75. Openings 76 are provided along the stitching 72 for admitting straps therethrough during use. A tear cord 77 can also be provided in the blanket 71 adjacent the stitching 72 so that the blanket 71 can be removed easily if desired.

The blanket 71 can comprise, for example, a silver rescue-type blanket, although this is not intended as a limitation. Exemplary measurements for the blanket 71 can comprise a width 78 of 36 in. and a length 79 of 60 in. The blanket 71 can be positioned so that access is still available to one of the patient's arms for treatment and measurement devices.

Yet another embodiment of a backboard cover 80 (FIG. 7) includes lumbar support system 81 that comprises a pocket 82 that is affixed via, for example, stitching to a bottom surface 84 of the cover 80. The pocket 82 is preferably positioned in a middle section 85 of the cover 80, and has an opening 86 for admitting an air bladder 87 having an inflation element 88 such as known in the art that extends outside the pocket 82. Thus, in use, the air bladder 87 can be inflated to a desired level for improving patient stability and comfort.

A further embodiment of a backboard cover 90 (FIG. 8) includes at a head portion 91 an adhesive element 92 covered with a cover sheet 93 that can be peeled away to reveal the adhesive element 92. The adhesive element 92 is intended for use with a CID system for subsequent addition if needed. The adhesive element 92 can also have adhesive on a rear side 94 to effect adhesion to a backboard in use.

An additional embodiment of a backboard cover 100 (FIG. 9) comprises, on a rear surface 101 of the sheet's upper portion 105, a pocket 102 for holding an element 103 comprising a plurality of fluid-filled bubbles 104, such as, but not intended to be limited to, a sheet of material such as "bubble wrap." This element 103 is for providing full body spinal support for stabilization and comfort. The pocket 102 can comprise a skid-resistant material for decreasing a chance of slippage of the cover 100.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A cover for a backboard for carrying a patient thereon comprising:

a sheet of flexible material having an upper portion dimensioned for covering a top surface of the backboard, and means for retaining the sheet on the backboard, the retaining means extending over a section of a bottom surface of the backboard;

first affixing means adjacent to a top edge of the upper portion for attaching a cervical immobilization device thereto; and second affixing means on a rear surface of the upper portion generally opposite the first affixing means for attachment to the backboard top surface.

2. The backboard cover recited in claim 1, wherein the sheet defines a plurality of sheet apertures, at least two of which positioned to overlie at least two handhold apertures extending through the backboard from the backboard top surface through to the backboard bottom surface.

3. The backboard cover recited in claim 2, wherein the apertures comprise perforated slots.

4. The backboard cover recited in claim 3, further comprising a reinforcing means positioned about a periphery of each slot.

5. The backboard cover recited in claim 1, wherein the sheet-retaining means comprises an upper and a lower pocket, the upper pocket joined to a top edge and a top section of opposed side edges of the upper portion, the lower pocket joined to a bottom edge and a bottom section of the opposed side edges of the upper portion.

6. The backboard cover recited in claim 5, wherein the upper and the lower pocket further have at least one aperture positioned to underlie a handhold aperture in the backboard.

7. The backboard cover recited in claim 5, wherein the upper and the lower pocket each has an elasticized inner edge for assisting in fitting the sheet to the backboard.

8. The backboard cover recited in claim 1, wherein the upper portion rear surface further comprises a non-skid element.

9. The backboard cover recited in claim 8, wherein the non-skid element comprises a rubberized element.

10. The backboard cover recited in claim 1, further comprising a blanket affixed along one side edge to a side edge of the sheet upper portion.

11. The backboard cover recited in claim 10, further comprising apertures positioned along the joined side edges of the blanket and the sheet upper portion, for providing access to a strap therethrough in use.

12. The backboard cover recited in claim 1, wherein the first affixing means comprises a hook-and-latch element for affixing a corresponding hook-and-latch element thereto.

13. The backboard cover recited in claim 1, wherein the sheet comprises a polypropylene material.

14. The backboard cover recited in claim 1, wherein the sheet upper portion has a lower region thereof comprising a stretchable material for assisting in fitting the sheet to the backboard.

15. The backboard cover recited in claim 1, further comprising the cervical immobilization device comprising:

a base affixable to the pad;

a pair of head restraints adjustably positionable atop and adjacent opposed side edges of the base in spaced relation from each other for placement on opposite sides of a head of a patient; and a chin strap affixed to the base for placement under a chin of the patient.

16. The backboard cover recited in claim 1, further comprising a lumbar support device affixable to a middle section of the sheet upper portion, the lumbar support inflatable for improving patient back stability and comfort.

17. The backboard cover recited in claim 1, wherein the first affixing means comprises an adhesive element positioned at a head portion thereof for affixing the cervical immobilization device thereto in use.

18. The backboard cover recited in claim 1, wherein the rear surface of the sheet upper portion comprises a pocket therein, and further comprising a sheet having a plurality of fluid-filled bubbles therein, for providing patient spinal support in use.

19. The backboard cover recited in claim 1, wherein the second affixation means is an adhesive element.

20. A cover for a backboard for carrying a patient thereon comprising:

a sheet of flexible material having an upper portion dimensioned for covering a longitudinally central top surface of the backboard, the upper portion dimensioned to extend between side handholds of the backboard along a central portion thereof, and means for retaining the sheet on the backboard, the retaining means extending over a section of the backboard bottom surface;

first affixing means adjacent to a top edge of the upper portion for attaching a cervical immobilization device thereto; and second affixing means on a rear surface of the upper portion generally opposite the first affixing means for attachment to the backboard top surface.

21. The backboard cover recited in claim 20, wherein the retaining means comprises downward-facing top and bottom pockets formed with the sheet upper portion, each having a width sufficient to encompass upper and lower ends of the backboard.

22. The backboard cover recited in claim 21, wherein at least one of the top and the bottom pockets comprise an elasticized edge.

23. A method of transporting an injured patient using the cover of claim 1, the method comprising: positioning the cover on the backboard; attaching, via the first affixing means, the cervical immobilization device adjacent to the top edge of the upper portion of the cover; attaching, via the second affixing means generally opposite the first affixing means, the rear surface of the upper portion to the backboard top surface; and positioning a patient on the cover.

24. The method recited in claim 23, wherein attaching the cervical immobilization device includes, prior to the patient-positioning step, affixing a base of the cervical immobilization device to the first affixing means, and, following the patient-positioning step, positioning a pair of head restraints of the cervical immobilization device on opposite sides of a head of the patient, affixing the pair of head restraints to the base, and affixing a chin strap under a chin of the patient.

* * * * *